(12) United States Patent
Whitehurst et al.

(10) Patent No.: US 7,890,177 B1
(45) Date of Patent: *Feb. 15, 2011

(54) DEVICE AND THERAPY FOR ERECTILE DYSFUNCTION AND OTHER SEXUAL DYSFUNCTION

(75) Inventors: Todd K Whitehurst, Santa Clarita, CA (US); James P McGivern, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 872 days.

This patent is subject to a terminal disclaimer.

(21) Appl. No.: 11/338,335

(22) Filed: Jan. 24, 2006

Related U.S. Application Data

(60) Division of application No. 10/712,853, filed on Nov. 12, 2003, now Pat. No. 7,006,870, which is a continuation-in-part of application No. 09/799,988, filed on Mar. 6, 2001, now Pat. No. 6,650,943.

(60) Provisional application No. 60/195,533, filed on Apr. 7, 2000.

(51) Int. Cl.
*A61N 1/08* (2006.01)
*A61N 1/00* (2006.01)

(52) U.S. Cl. .................................. 607/39; 607/143

(58) Field of Classification Search ............... 607/39, 607/143, 2; 128/788
See application file for complete search history.

(56) References Cited

U.S. PATENT DOCUMENTS

| | | | |
|---|---|---|---|
| 3,542,870 A | 11/1970 | Fourneau et al. | |
| 3,850,161 A | 11/1974 | Liss | |
| 3,881,495 A | 5/1975 | Pannozzo et al. | |

(Continued)

FOREIGN PATENT DOCUMENTS

WO   WO-97/02794 A1   1/1997

(Continued)

OTHER PUBLICATIONS

Non-Final Office Action received in U.S. Appl. No. 11/338,006, filed Sep. 19, 2009.

(Continued)

*Primary Examiner*—Daniel L Robinson
(74) *Attorney, Agent, or Firm*—Wong, Cabello Lutsch, Rutherford & Brucculeri, LLP

(57) ABSTRACT

An implantable stimulator(s) with at least one infusion outlet and/or at least one electrode, is implanted with the outlet(s) and/or electrode(s) located adjacent to a pudendal nerve(s) and potentially other nerve(s) innervating the reproductive organs, such as the cavernous nerve(s). Stimulation of such nerve(s) is provided via stimulating drugs and/or electrical stimulation as a therapy for erectile dysfunction. The stimulator uses a power source/storage device, such as a rechargeable battery. Periodic recharging of such a battery is accomplished, for example, by inductive coupling with an external appliance. The stimulator provides means of stimulating a nerve(s) when desired, without the need for external appliances during the stimulation session. When necessary, external appliances are used for the transmission of data to and/or from the stimulator(s) and for the transmission of power. The system is capable of open- and closed-loop operation. In closed-loop operation, at least one implant includes a sensor, and the sensed condition is used to adjust stimulation parameters.

20 Claims, 7 Drawing Sheets

U.S. PATENT DOCUMENTS

| | | |
|---|---|---|
| 3,941,136 A | 3/1976 | Bucalo |
| 4,121,592 A | 10/1978 | Whalley |
| 4,167,466 A | 9/1979 | Orr, Jr. et al. |
| 4,232,679 A | 11/1980 | Schulman |
| 4,397,860 A | 8/1983 | Chapleo et al. |
| 4,408,608 A | 10/1983 | Daly et al. |
| 4,467,809 A | 8/1984 | Brighton |
| 4,481,950 A | 11/1984 | Duggan |
| 4,542,753 A | 9/1985 | Brenman et al. |
| 4,585,005 A | 4/1986 | Lue et al. |
| 4,590,946 A | 5/1986 | Loeb |
| 4,602,624 A | 7/1986 | Naples et al. |
| 4,608,985 A | 9/1986 | Crish et al. |
| 4,628,942 A | 12/1986 | Sweeney et al. |
| 4,649,936 A | 3/1987 | Ungar et al. |
| 4,669,475 A | 6/1987 | Turner |
| 4,702,254 A | 10/1987 | Zabara |
| 4,793,353 A | 12/1988 | Borkan |
| 4,867,164 A | 9/1989 | Zabara |
| 5,059,603 A | 10/1991 | Rubin |
| 5,188,104 A | 2/1993 | Wernicke et al. |
| 5,193,539 A | 3/1993 | Schulman et al. |
| 5,193,540 A | 3/1993 | Schulman et al. |
| 5,199,430 A | 4/1993 | Fang et al. |
| 5,211,129 A | 5/1993 | Taylor et al. |
| 5,215,086 A | 6/1993 | Terry, Jr. et al. |
| 5,236,904 A | 8/1993 | Gerstenberg et al. |
| 5,299,569 A | 4/1994 | Wernicke et al. |
| 5,305,445 A | 4/1994 | Nishikawa |
| 5,312,439 A | 5/1994 | Loeb |
| 5,314,456 A | 5/1994 | Cohen |
| 5,314,458 A | 5/1994 | Najafi et al. |
| 5,324,316 A | 6/1994 | Schulman et al. |
| 5,330,515 A | 7/1994 | Rutecki et al. |
| 5,332,401 A | 7/1994 | Davey et al. |
| 5,358,514 A | 10/1994 | Schulman et al. |
| 5,366,490 A | 11/1994 | Edwards et al. |
| 5,400,784 A | 3/1995 | Durand et al. |
| 5,405,367 A | 4/1995 | Schulman et al. |
| 5,439,938 A | 8/1995 | Snyder et al. |
| 5,454,840 A | 10/1995 | Krakovsky et al. |
| 5,505,201 A | 4/1996 | Grill, Jr. et al. |
| 5,513,636 A | 5/1996 | Palti et al. |
| 5,515,848 A | 5/1996 | Corbett, III et al. |
| 5,529,574 A | 6/1996 | Frackelton |
| 5,531,778 A | 7/1996 | Maschino et al. |
| 5,547,467 A | 8/1996 | Pliquett et al. |
| 5,561,154 A | 10/1996 | Bellamy et al. |
| 5,571,118 A | 11/1996 | Boutos |
| 5,571,148 A | 11/1996 | Loeb et al. |
| 5,576,290 A | 11/1996 | Hadley |
| 5,594,032 A | 1/1997 | Gonzalez-Cadavid et al. |
| 5,634,462 A | 6/1997 | Tyler et al. |
| 5,649,970 A | 7/1997 | Loeb et al. |
| 5,700,282 A | 12/1997 | Zabara |
| 5,713,922 A | 2/1998 | King |
| 5,752,979 A | 5/1998 | Benabid et al. |
| 5,755,750 A | 5/1998 | Petruska et al. |
| 5,775,331 A | 7/1998 | Raymond et al. |
| 5,800,493 A | 9/1998 | Stevens et al. |
| 5,807,306 A | 9/1998 | Shapland et al. |
| 5,895,416 A | 4/1999 | Barreras, Sr. et al. |
| 5,899,933 A | 5/1999 | Bhadra et al. |
| 5,916,569 A | 6/1999 | Spencer et al. |
| 5,919,187 A | 7/1999 | Guglielmi et al. |
| 5,938,584 A | 8/1999 | Ardito et al. |
| 5,995,868 A | 11/1999 | Dorfmeister et al. |
| 6,016,452 A | 1/2000 | Kasevich |
| 6,021,347 A | 2/2000 | Herbst et al. |
| 6,035,237 A | 3/2000 | Schulman et al. |
| 6,037,346 A | 3/2000 | Doherty, Jr. et al. |
| 6,044,456 A | 3/2000 | Murty et al. |
| 6,051,017 A | 4/2000 | Loeb et al. |
| 6,055,456 A | 4/2000 | Gerber |
| 6,058,331 A | 5/2000 | King |
| 6,104,956 A | 8/2000 | Naritoku et al. |
| 6,115,637 A | 9/2000 | Lennox et al. |
| 6,154,678 A | 11/2000 | Lauro |
| 6,161,044 A | 12/2000 | Silverstone |
| 6,162,219 A | 12/2000 | Nilsson et al. |
| 6,164,284 A | 12/2000 | Schulman et al. |
| 6,167,305 A | 12/2000 | Cammilli et al. |
| 6,169,924 B1 | 1/2001 | Meloy et al. |
| 6,177,404 B1 | 1/2001 | DeFeo-Jones et al. |
| 6,178,349 B1 | 1/2001 | Kieval |
| 6,185,452 B1 | 2/2001 | Schulman et al. |
| 6,190,381 B1 | 2/2001 | Olsen et al. |
| 6,198,970 B1 | 3/2001 | Freed et al. |
| 6,205,359 B1 | 3/2001 | Boveja |
| 6,208,894 B1 | 3/2001 | Schulman et al. |
| 6,214,032 B1 | 4/2001 | Loeb et al. |
| 6,216,045 B1 | 4/2001 | Black et al. |
| 6,226,552 B1 | 5/2001 | Staunton et al. |
| 6,251,436 B1 | 6/2001 | Drizen et al. |
| 6,266,564 B1 | 7/2001 | Hill et al. |
| 6,296,639 B1 | 10/2001 | Truckai et al. |
| 6,319,194 B1 | 11/2001 | Wulf |
| 6,341,236 B1 | 1/2002 | Osorio et al. |
| 6,366,808 B1 | 4/2002 | Schroeppel et al. |
| 6,366,818 B1 | 4/2002 | Bolmsjo |
| 6,391,026 B1 | 5/2002 | Hung et al. |
| 6,402,689 B1 | 6/2002 | Scarantino et al. |
| 6,472,991 B1 | 10/2002 | Schulman et al. |
| 6,505,078 B1 | 1/2003 | King et al. |
| 6,526,318 B1 | 2/2003 | Ansarinia |
| 6,560,490 B2 | 5/2003 | Grill et al. |
| 6,597,954 B1 | 7/2003 | Pless et al. |
| 6,600,954 B2 | 7/2003 | Cohen et al. |
| 6,642,274 B1 | 11/2003 | Neal |
| 6,650,943 B1 * | 11/2003 | Whitehurst et al. .......... 607/39 |
| 6,712,753 B2 | 3/2004 | Manne |
| 6,782,292 B2 | 8/2004 | Whitehurst |
| 6,826,428 B1 | 11/2004 | Chen et al. |
| 6,862,479 B1 | 3/2005 | Whitehurst et al. |
| 6,885,895 B1 | 4/2005 | Whitehurst et al. |
| 6,907,295 B2 | 6/2005 | Gross et al. |
| 6,928,320 B2 | 8/2005 | King |
| 7,006,870 B1 | 2/2006 | Whitehurst et al. |
| 7,054,692 B1 | 5/2006 | Whitehurst et al. |
| 7,203,548 B2 | 4/2007 | Whitehurst et al. |
| 2001/0003799 A1 | 6/2001 | Boveja |
| 2001/0039257 A1 | 11/2001 | Adams et al. |
| 2002/0016615 A1 | 2/2002 | Dev et al. |
| 2002/0022873 A1 | 2/2002 | Erickson et al. |
| 2002/0026188 A1 | 2/2002 | Balbierz et al. |
| 2002/0055779 A1 | 5/2002 | Andrews |
| 2002/0099256 A1 | 7/2002 | Manne |
| 2002/0099419 A1 | 7/2002 | Cohen et al. |
| 2002/0102707 A1 | 8/2002 | Harrow et al. |
| 2002/0161415 A1 | 10/2002 | Cohen et al. |
| 2002/0193859 A1 | 12/2002 | Schulman et al. |
| 2003/0018365 A1 | 1/2003 | Loeb |
| 2003/0027751 A1 | 2/2003 | Kovesdi et al. |
| 2003/0045909 A1 | 3/2003 | Gross et al. |
| 2003/0045914 A1 | 3/2003 | Cohen et al. |
| 2003/0050677 A1 | 3/2003 | Gross et al. |
| 2003/0083698 A1 | 5/2003 | Whitehurst et al. |
| 2003/0100933 A1 | 5/2003 | Ayal et al. |
| 2003/0203890 A1 | 10/2003 | Steiner et al. |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0172089 A1 | 9/2004 | Whitehurst et al. |

| | | | |
|---|---|---|---|
| 2004/0243182 | A1 | 12/2004 | Cohen et al. |
| 2004/0243185 | A1 | 12/2004 | Weiss et al. |
| 2005/0101878 | A1 | 5/2005 | Daly et al. |

FOREIGN PATENT DOCUMENTS

| | | | |
|---|---|---|---|
| WO | WO-97/39760 | A1 | 10/1997 |
| WO | WO-98/37926 | A1 | 9/1998 |
| WO | WO-98/43700 | A1 | 10/1998 |
| WO | WO-98/43701 | A1 | 10/1998 |
| WO | WO-01/60445 | A2 | 8/2001 |
| WO | WO-01/60445 | A3 | 8/2001 |
| WO | WO-01/76690 | A1 | 10/2001 |
| WO | WO-02/058782 | A2 | 8/2002 |
| WO | WO-02/058782 | A3 | 8/2002 |
| WO | WO-02/092165 | A1 | 11/2002 |
| WO | WO-03/018113 | A1 | 3/2003 |

OTHER PUBLICATIONS

U.S. Appl. No. 10/119,561, Official Communication: "Notice Of Allowance and Fee(s) Due" mailed on Dec. 17, 2004 (9 pages).
U.S. Appl. No. 11/112,630, Official Communication mailed Oct. 31, 2008 (7 pages).
U.S. Appl. No. 11/112,630, Official Communication mailed Feb. 25, 2008 (7 pages).
U.S. Appl. No. 10/133,771, Official Communication mailed Dec. 29, 2003 (6 pages).
U.S. Appl. No. 10/133,771, Official Communication mailed Jul. 23, 2004 (4 pages).
U.S. Appl. No. 10/133,771, Official Communication mailed Dec. 1, 2004 (4 pages).
U.S. Appl. No. 10/133,768, Official Communication mailed Jul. 22, 2004 (7 pages).
U.S. Appl. No. 10/133,768, Official Communication mailed Dec. 29, 2003 (7 pages).
U.S. Appl. No. 10/133,768, Official Communication mailed Dec. 2, 2004 (4 pages).
U.S. Appl. No. 11/112,630, Official Communication mailed Apr. 8, 2009 (5 pages).
U.S. Appl. No. 10/176,743, Official Communication mailed Aug. 23, 2005 (14 pages).
U.S. Appl. No. 10/176,743, Official Communication mailed Jan. 19, 2006 (15 pages).
U.S. Appl. No. 10/176,743, Official Communication mailed Jul. 21, 2006 (14 pages).
Ando et al., "Treatment of Solid Tumor By A Direct Electric Current", Japanese Journal of Cancer and Chemotherapy, Oct. 1999, 26(12):1856-1859.
Berendson et al., "Electrochemical Aspects Of Treatment Of Tissue With Direct Current," European Journal of Surgery, 1994, Supplement 574:111-115.
Griffin et al., "Low-Level Direct Electrical Current Therapy For Hepatic Metastases. I. Preclinical Studies On Normal Liver", British Journal of Cancer, Jul. 1995, 72(1)31-34.
Junemann et al., "Neurophysiology Of Penile Erection", Urological Research, 1989, 17:213- 217.
Plensicar, A. et al., "Treatment Of Human Melanoma Skin Lesions With Low Level Direct Electric Current: An Assessment Of Clinical Experience Following A Preliminary Study in Five Patents", European Journal Of Surgery, 1994, Supplement 574:45-49.
Shi et al., "Clinical Evaluation Of Several Tumor Markers in The Diagnosis Of Primary Hepatic Cancer", Zhonghua Zhong Liu Za Zhi, Nov. 1998, 20(6):437-439.
Schulman et al., "Simultaneous Bilateral Obturator Nerve Stimulation During Transurethral Electrovaporization Of The Prostate", Journal Of Clinical Anesthesiology, Sep. 1998, 10(6):518-521.
Taylor et al., "Ablation Of Neoplasia By Direct Current", British Journal Of Cancer, Aug. 1994, 70(2):342-345.
Turler et al., "Local Treatment Of Hepatic Metastases With Low-Level Direct Electric Current: Experimental Results", Journal of Gastroenterology, Mar. 2000, 35(3):322-328.
Yen et al. "Electrochemical Treatment Of Human KB Cells In Virto", Journal Bioelectromagnetics, 1999, 20(1):24-41.

Steers, W.D., "Neural Pathways and Central Sites Involved in Penile Erection Neuroanatomy and Clinical Implications," 2000, Neuroscience and Biobehavioral Reviews, 24:507-516.
U.S. Appl. No. 11/141,443, Official Communication mailed Aug. 15, 2007 (9 pages).
U.S. Appl. No. 11/141,443, Official Communication mailed Nov. 21, 2008 (12 pages).
U.S. Appl. No. 60/383,157 filed on May 23, 2002 (47 pages).
U.S. Appl. No. 11/141,443, Official Communication mailed Mar. 11, 2009 (12 pages).
Annich et al', "Reduced Platelet Activation and Thrombosis in Extracorporeal Circuits Coated with Nitric Oxide Release Polymers," Crit Care Med, Apr. 28, 2000, pp. 915-920.
Ballard et al., "Effects of Sildenafil on the Relaxation of Human Corpus Cavernosum Tissue in Vitro and on the Activities of Cyclic Nucleotide Phosphodiesterase Isozymes," The Journal of Urology 159, 1998, pp. 2164-2171.
Cameron et al., "Micromodular Implants to Provide Electrical Stimulation of Paralyzed Muscles and Limbs," IEEE Transactions on Biomedical Engineering, vol. 44, No. 9, Sep. 1997, pp. 781-790.
Carter et al., "Effect of the Selective Phosphodiesterase Type Inhibitor Sildenafil on Erectile Function in the Anesthetized Dog," The Journal of Urology 160, 1998, pp. 781-790.
Creasey et al., "Electrical Stimulation of Sacral Roots for Micturition After Spinal Cord Injury," Urologic Clinics of North America 20, Aug. 1993, pp. 505-515.
Goldstein et al., "Oral Sildenafil in the Treatment of Erectile Dysfunction," The New England Journal of Medicine 338, 1998, pp. 1397-1404.
Kim et al., "Alpha-Adrenergic Receptor Blockade by Phentolamine Increases the Efficacy of Vasodilators in Penile Corpus Cavernosum," International Journal Impotence Research, vol. 12, Suppl 1, Mar. 2000, pp. 26-36.
Lue et al., "Electrostimulation and Penile Erection," Urol. Int. 40, 1985, pp. 60-64.
Martinez-Pineiro et al., "Rat Model for the Study of Penile Erection: Pharmacologic and Electrical-Stimulation Parameters," Eur Urol 25, 1994, pp. 62-70.
Moreland et al., "Sildenafil, A Novel Inhibitor of Phosphodiesterase Type 5 in Human Corpus Cavernosum Smooth Muscle Cells," Life sciences 62, 1998, pp. 309-318.
Mowery et al., "Preparation and Characterization of Hydrophobic Polymeric Films that are Thromboresistant via Nitric Oxide Release," Biomaterials 21, Jan. 2000, pp. 9-21.
Shafik, "Cavernous Nerve Stimulation through an Extrapelvic subpubic Approach: Role in Penile Erection," Eur Urol 26, 1994, pp. 98-102.
Shafik, "Extrapelvic Cavernous Nerve Stimulation in Erectile Dysfunction. Human Study," Andrologia 28, May - Jun. 1995, pp. 151-156.
Shafik, "Perineal Nerve Stimulation: Role in Penile Erection," International Journal of impotence Research 9, Mar. 1997, pp. 11-18.
Stief, "The Influence of Anterior Roots stimulation (S2) in Deafferented Spinal cord Injury men On Cavernous Electrical Activity," The Journal of Urology 148, Jul. 1992, pp. 107-110.
Tai, "Penile Erection Produced by microstimulation of the Sacral Spinal cord of the Cat," IEEE Transactions Rehabilitation Engineering, vol. 6, No. 4, Dec. 1998, pp. 374-381.
Matsumoto et al., alpha-Adrenoceptor-mediated Penile Erection in Dogs: In vivo and in vitro Observations, 2000, Journal of Smooth Muscle Research, 36, 169-179.
Doxey et al., Inhibitory Effects of Clonidine on Responses to Sympathetic Nerve Stimulation in the Pithed Rat, 1977, British Journal of Pharmacology, 61, 559-566.
Stanford et al., "Urinary and Sexual Function After Radical Prostatectomy for Clinically Localized Prostate Cancer: The Prostate Cancer Outcomes Study," The Journal Of Urology 148, Jul. 1992, 107-110.
Yen et al. "Electrochemical Treatment Of Human KB Cells In Virto", Journal Bioelectromagnetics, 1999, 20(1):34-41.
Carter et al., "Effect of the Selective Phosphodiesterase Type Inhibitor Sildenafil on Erectile Function in the Anesthetized Dog," The Journal of Urology 160, 1998, pp. 242-246.

Stanford et al., "Urinary and Sexual Function After Radical Prostatectomy for Clinically Localized Prostate Cancer: The Prostate Cancer Outcomes Study," Journal Of The American Medical Association (JAMA) (Jan. 2000), 283(3), 354-360.

U.S. Appl. No. 11/112,630, Official Communication mailed Jun. 19, 2009 (3 pages).

U.S. Appl. No. 11/141,443 Official Communication mailed Jul. 30, 2009 (23 pages).

Maggi, C.A., "Nervous Control of the Urogenital System: Automonic Nervous System," Taylor & Francis, vol. 3, May 20, 1993, pp. 39-40, 69-71, 82, 86 and 87.

Cohen, H., "Neuroscience for Rehabilitation," Lippinkcott Williams & Wilkins, Jan. 5, 1999, pp. 296-299.

Lue, T.F. et al, "Physiology of Penile Erection," Digital Urology Journal, Feb. 21, 1999, pp. 1-11.

* cited by examiner

DEVICE AND THERAPY FOR ERECTILE DYSFUNCTION AND OTHER SEXUAL DYSFUNCTION

The present application is a divisional of U.S. patent application Ser. No. 10/712,853, filed Nov. 12, 2003, which application is now U.S. Pat. No. 7,006,870, issued Feb. 28, 2006, which in turn is a continuation-in-part of application Ser. No. 09/799,988, filed Mar. 6, 2001, now U.S. Pat. No. 6,650,943, issued Nov. 18, 2003, which in turn claims the benefit of U.S. Provisional Patent Application Ser. No. 60/195,533, filed Apr. 7, 2000. These applications and this patent are incorporated herein by reference in their entirety.

FIELD OF THE INVENTION

The present invention generally relates to implantable stimulator systems, and more particularly relates to utilizing such devices to deliver one or more therapeutic drugs and/or electrical stimulation as a therapy for erectile dysfunction.

BACKGROUND

Recent estimates suggest that the number of U.S. men with erectile dysfunction may be near 10 to 20 million, and inclusion of individuals with partial erectile dysfunction increases the estimate to about 30 million. The male erectile response is initiated by the action of neurons, or nerve cells (i.e., neuronal action), and maintained by a complex interplay between events involving blood vessels (i.e., vascular events) and events involving the nervous system (i.e., neurological events).

The part of the nervous system that regulates involuntary action (e.g., the intestines, heart, glands) is called the autonomic nervous system. The autonomic nervous system is divided into two mutually antagonistic, physiologically and anatomically distinct systems: the sympathetic nervous system and the parasympathetic nervous system. The sympathetic nervous system originates in the thoracic and lumbar regions of the spinal cord, and in general, opposes the physiological affects of the parasympathetic nervous system. For instance, the sympathetic nervous system will tend to reduce digestive secretions or speed up the heart, usually when an individual is in an active state. The parasympathetic nervous system originates in the brain stem and the lower part of the spinal cord, and, in general, opposes the physiological effects of the sympathetic nervous system. Thus, the parasympathetic nervous system will tend to stimulate digestive secretions or slow the heart usually when an individual is in a relaxed state.

It is parasympathetic neuronal action that initiates the male erectile response. Specifically, this parasympathetic input originates from the nerve plexus (i.e., a structure in the form of a network) called the pelvic splanchnic nerve plexus. The pelvic splanchnic nerve plexus is comprised of branches from the second, third, and fourth sacral nerves (from the lower part of the spinal cord) that intertwine with the inferior hypogastric plexus, which is a network of nerves in the pelvis. The cavernous nerves (designated greater and lesser) are derived from the pelvic splanchnic nerves, and supply parasympathetic fibers to the corpora cavernosa and corpus spongiosum, the erectile tissue in the penis containing large interspaces capable of being distended with blood.

This activity allows erection by relaxation of smooth muscle (i.e., muscle in the walls of internal organs, blood vessels, hair follicles, etc., that contracts without voluntary control) and dilation of the helicine arteries, which are coiled arteries found in the erectile tissue of the penis. The dilation of the arteries causes greatly increased blood flow through the erectile tissue, which leads to expansion of the three cylinders of erectile tissue in the penis (i.e., the corpora cavernosa and the corpus spongiosum). As the corpora cavernosa and the corpus spongiosum expand, the venous structures draining the penis are compressed against the fascia surrounding each of the erectile tissues (i.e., the tunica albuginea of the corpora cavernosa and the tunica albuginea of the corpus spongiosum). Thus, the outflow of blood is restricted, and the internal pressure increases. This vein-obstruction process is referred to as the corporal veno-occlusive mechanism.

Conversely, the flaccid state is maintained by continuous sympathetic (alpha-adrenergic) nervous system stimulation of the penile blood vessels and trabecular smooth muscle. Constriction of the smooth muscle and helicine arteries induced by sympathetic innervation from the hypogastric nerves—e.g., from certain nerves of the inferior hypogastric plexus—may make the penis flaccid.

Erectile dysfunction has a number of causes, both physiological and psychological, and in many patients the disorder may be multifactorial. The causes include several that are essentially neurologic in origin. Damage to the pathways used by the autonomic nervous system to innervate the penis may interrupt "psychogenic" erection initiated by the central nervous system. Psychogenic erection has a mental or emotional origin, rather than a physical basis. Lesions (e.g., injury, infection, or disease) of the somatic nervous pathways (i.e., any of the nerves associated with sensation or motion) may impair reflexogenic erections (i.e., involuntary, instinctive physiological response to a stimulus) and may interrupt tactile sensation needed to maintain psychogenic erections. Spinal cord lesions may produce varying degrees of erectile failure depending on the location and severity of the lesions.

Not only lesions affect erectile ability; disorders leading to peripheral neuropathy may also impair neuronal innervation of the penis. Peripheral neuropathy is a disorder or abnormality of the part of the nervous system constituting the nerves outside the central nervous system and including the cranial nerves, the spinal nerves, and the sympathetic and parasympathetic nervous systems. Peripheral neuropathy may also impair neuronal innervation of the sensory afferents—the nerves that conduct impulses from the periphery of the body to the brain or spinal cord, transmitting impulses from sense organs to nerve centers. Peripheral neuropathy is a potential sequela of a number of diseases, e.g., diabetes mellitus.

The endocrine system (glands such as the thyroid, adrenal, or pituitary, having hormonal secretions that pass directly into the bloodstream), particularly the production of androgens (steroid hormones, such as testosterone or androsterone, that control the development and maintenance of masculine characteristics), appears to play a role in regulating sexual interest, and may also play a role in erectile function.

In men of all ages, erectile failure may diminish willingness to initiate sexual relationships because of fear of inadequate sexual performance or rejection. Because males, especially older males, are particularly sensitive to the social support of intimate relationships, withdrawal from these relationships because of such fears may have a negative effect on their overall health.

Some forms of erectile dysfunction are treated with medication, with varying degrees of success. For instance, the well-publicized oral medication VIAGRA® (active ingredient sildenafil citrate) requires an hour to exert its full effects, and it may have significant side effects such as abnormal vision, flushing, headache, and diarrhea.

Intracavernosal injection therapy, in which a patient injects vasodilator substances (e.g., alprostadil, papaverine, phentolamine) into the corpora of the penis, suffers a high rate of patient dropout, as does therapeutic application of vacuum constriction devices. Several forms of penile prostheses are available, including semirigid, malleable, and inflatable, but these have significant problems with mechanical failure, infection, and device erosion.

Alprostadil has been used in the UK to treat impotence since 1994. Alprostadil is identical to a substance called prostaglandin-E 1 that occurs naturally in the penis and is involved in the natural erection process. Alprostadil relaxes the blood vessels and muscles in the erectile tissue of the penis allowing increased blood flow, the basis of a normal erection.

Various stimulation devices have been proposed for treating erectile dysfunction. Some devices stimulate through the skin, such as intrarectal stimulation devices. Other devices require significant surgical procedures for placement of electrodes, leads, and processing units. These devices may also require an external apparatus that needs to be strapped or otherwise affixed to the skin. While several patents exist regarding stimulators for treatment of erectile dysfunction, the inventors know of no chronic, fully implantable neurostimulator device that is commercially available.

BRIEF SUMMARY

The invention disclosed and claimed herein provides systems and methods for chronically stimulating nerves derived from the pelvic splanchnic plexus, such as the pudendal and cavernous nerves. Stimulation of the cavernous nerve(s) and/or pudendal nerve(s) may be an effective therapy for erectile dysfunction. Such therapy may be provided via stimulating drugs and/or electrical stimulation. For instance, in one embodiment, excitatory drugs are infused to activate the pudendal nerve while optional excitatory stimulation (via drug or electrical stimulation) is applied to one or more of the cavernous nerves.

The treatment provided by the invention may be carried out by one or more system control units (SCUs). In some forms of an SCU, one or more infusion outlets and/or catheters are surgically implanted to infuse drug(s) from an implantable pump. Additionally or alternatively, one or more electrodes are surgically implanted to provide electrical stimulation from an implantable signal/pulse generator (IPG). When necessary and/or desired, an SCU may provide both electrical stimulation and one or more stimulating drugs. In other forms of an SCU, a miniature implantable neurostimulator (a.k.a., a microstimulator), such as a Bionic Neuron (also referred to as a BION® microstimulator) or the like, is implanted. For instance, a BION SCU(s) may be implanted adjacent the pudendal nerve at the pudendal canal. The systems of the invention may also include one or more sensors for sensing the need for or the response to stimulation.

A single SCU may be implanted, or two or more SCUs may be implanted to achieve greater stimulation of the nerve fibers (e.g., all branches of the pudendal nerves). Alternatively, an SCU(s) may be implanted adjacent to parasympathetic targets, such as the greater and/or lesser cavernous nerves, proximal cavernous nerves, the prostatic plexus, the pelvic splanchnic nerves, or the second, third, and/or fourth sacral nerves (i.e., S2, S3, S4). In order to inhibit sympathetic input that, e.g., retards erection, an SCU(s) may also/instead be implanted adjacent to the hypogastric nerve, certain nerves of the inferior hypogastric plexus or its branches, or the sympathetic ganglia from which the hypogastric nerve is derived.

Stimulation and control parameters of the implanted SCU(s) are preferably adjusted to levels that are safe and efficacious with minimal discomfort. Different stimulation parameters have different effects on neural tissue, and parameters may be chosen to target specific neural populations and to exclude others. For example, when applied at relatively low frequencies (i.e., less than about 100 Hz), electrical stimulation typically has an excitatory effect, leading to increased neural activity of surrounding neural tissue. Conversely, relatively high frequency electrical stimulation (i.e., greater than about 100 Hz) generally has an inhibitory effect, leading to decreased neural activity.

According to one embodiment of the invention, the stimulation increases excitement of the somatic motor input to the penis, such as the pudendal nerve(s). According to another embodiment of the invention, the stimulation also increases excitement of the parasympathetic input to the penis. According to yet another embodiment of the invention, the stimulation also decreases excitement of the sympathetic input to the penis.

The SCU used with the present invention possesses one or more of the following properties, among other properties:
- at least one pump and at least one outlet for delivering a drug or drugs to surrounding tissue;
- optionally, at least one electrode for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry; and
- means for receiving and/or storing power within the SCU.

An SCU may operate independently, or in a coordinated manner with other implanted SCUs, other implanted devices, and/or with devices external to a patient's body. For instance, an SCU may incorporate means for sensing a patient's condition. Sensed information may be used to control the drug and/or electrical stimulation parameters of the SCU in a closed loop manner. The sensing and stimulating means may be incorporated into a single SCU, or a sensing means may communicate sensed information to at least one SCU with stimulating means.

Thus, the present invention provides a therapy for erectile and other sexual dysfunction that utilizes one or more SCUs, including minimally invasive miniature neurostimulators. Advantages of the present invention include, but are not required by or limited to, the system's monitoring and programming capabilities, the power source, storage, and transfer mechanisms, the activation of the device by the patient or clinician, the system's open and closed-loop capabilities and closed-loop capabilities coupled with sensing a need for and/or response to treatment, coordinated use of one or more stimulators, and the small size of the stimulator(s).

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
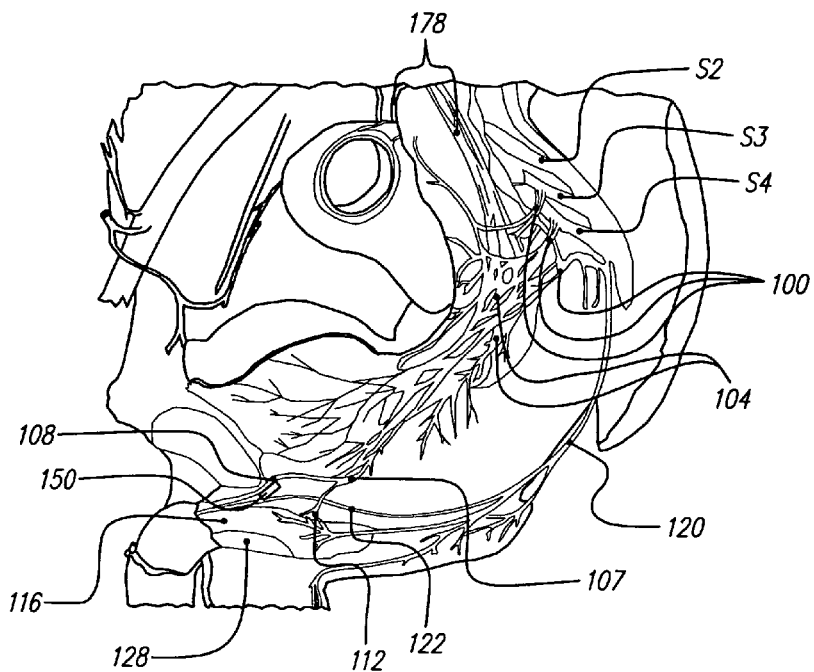
FIG. 1 depicts the nerves of the male pelvic viscera and surrounding anatomy, where a stimulation system of the present invention may be implanted.
Figure 2:
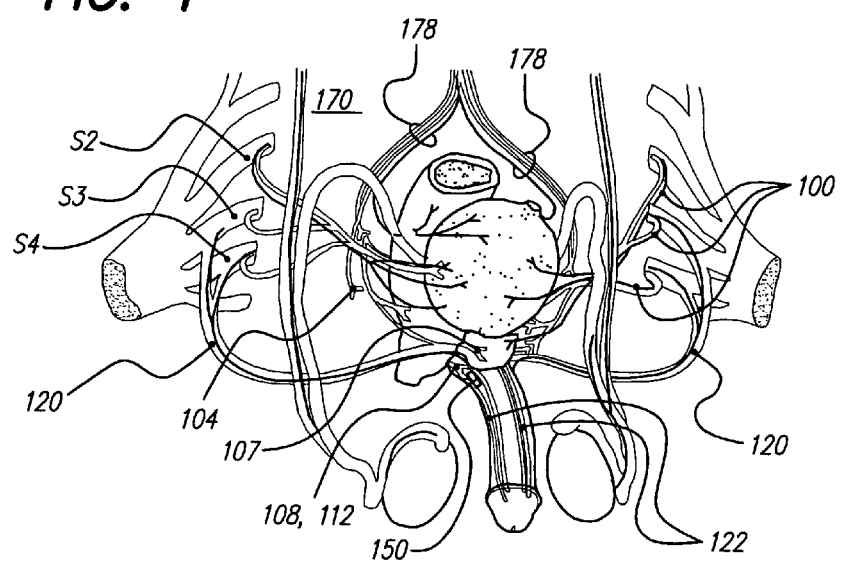
FIG. 2 illustrates the innervation of the male reproductive organs and a stimulation system of the present invention.

FIG. 1 depicts the nerves of a male pelvis, and FIG. 2 is a schematic representation of the sympathetic and parasympathetic fibers of the autonomic nervous system that are responsible for innervation of the male reproductive organs. The parasympathetic input that initiates and sustains the male erectile response arises from the second, third, and fourth sacral nerves (S2, S3, S4, respectively). In the pelvic splanchnic nerve plexus, the pelvic splanchnic nerves 100 are comprised of parasympathetic branches from S2, S3, and S4, that intertwine with the inferior hypogastric plexus 104. Greater cavernous nerve 108 and lesser cavernous nerve 112 are derived from the pelvic splanchnic nerves, and carry the parasympathetic input to the corpora cavernosa 116 and corpus spongiosum 128. Penile rigidity is related to the muscle tone of the striated bulbospongiosus and ischiocavernosus muscles, which are innervated by somatic motor fibers of the pudendal nerve 120 and/or branches of the pudendal nerve, such as the dorsal nerve of the penis 122.

Figure 3:
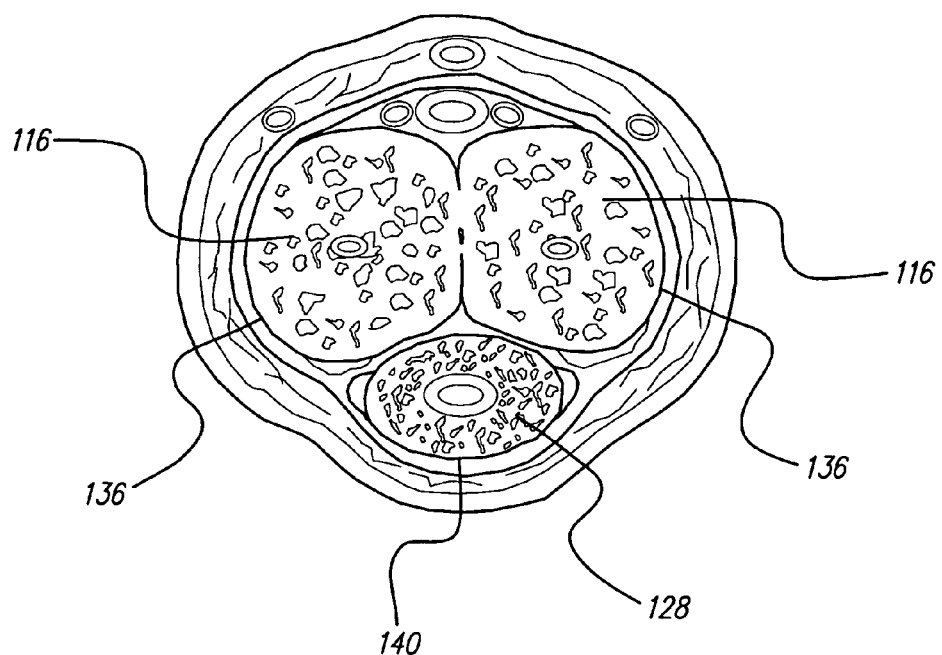
FIG. 3 is a section view through the body of a penis.

Referring next to FIG. 3, the corpora cavernosa 116 and the corpus spongiosum 128 are the spongy tissues that are engorged with blood during an erection. The corpora cavernosa 116 are paired tissue bodies that lie dorsally, while the corpus spongiosum 128 is located ventrally and surrounds the urethra. The parasympathetic signals carried to the corpora cavernosa 116 and corpus spongiosum 128 cause relaxation of smooth muscle surrounding the arteries and arterioles of the penis and dilation of the arteries and arterioles of the penis. The dilation of the arteries and arterioles causes increased blood flow through the erectile tissue, which leads to expansion of the corpora cavernosa 116 and corpus spongiosum 128. Due to this expansion, the venous structures draining the penis are compressed against the corpora cavernosa's tunica albuginea 136 and the corpus spongiosum's tunica albuginea 140. Thus, the outflow of blood is restricted, and the internal pressure increases.

The male erectile response begins with sexual stimulation, which triggers the parasympathetic nervous system to release neurotransmitters. Acetylcholine is the neurotransmitter believed to be responsible for triggering the chain of events that leads to a penile erection. The cavernous nerves release the neurotransmitter, which binds to the endothelial cells (thin flattened cells that line internal body cavities) of the arteries, causing the endothelial cells to synthesize and release nitric oxide (NO). NO diffuses out of the endothelial cells and into adjacent smooth muscle cells, where it binds to the enzyme soluble guanylyl cyclase (sGC), and activates the enzyme to convert guanosine triphosphate (GTP) to cyclic guanosine 3',5'-cyclic monophosphate (cGMP). The rate of production of cGMP in the smooth muscle cells has been observed to increase by at least 400 times due to the interaction of guanylyl cyclase and NO. The increased production of cGMP results in the amplification of the effects of cGMP on smooth muscle.

Smooth muscle relaxation in the corpus cavernosum is induced by cGMP. The relaxation of the smooth muscle in the corpus cavernosum allows blood to flow into the penis, where it becomes trapped, as described earlier. As long as cGMP remains in the smooth muscle tissue, the muscle is unable to contract. The degradation and subsequent disappearance of cGMP from the smooth muscle tissue results in contraction and normal blood flow into and out of the corpus cavernosum. Therefore, cGMP is the final product of several steps needed to initiate and maintain a penile erection.

The cGMP produced in the smooth muscle tissue of the corpus cavernosum is broken down after a short time. But as long as sexual stimulation continues, the degraded cGMP is continuously replaced by more NO-induced cGMP and erection continues. Cyclic nucleotide phosphodiesterases, specifically Type V (PDE5), breaks down cGMP to GMP by catalyzing a reaction that breaks the phosphodiester bond using $H_2O$. PDE5 thereby impedes the actions of cGMP in maintaining penile erection. Sildenafil works by inhibiting PDE5, thereby slowing degradation of cGMP.

Some believe there is a vascular phase and a muscular phase of erection. Reported in 1987, Junemann et al. employed selective cavernous and pudendal nerve stimulation to study the neurophysiological and neurovascular mechanisms of penile erection in six monkeys. [See Junemann, et al. "The physiology of penile erection. II. Neurophysiology of penile erection." (Article in German.) *Urologe A* 1987 Sep. 26(5):289-93.] Corporeal pressure recordings during different neurostimulation patterns confirmed that tumescence and erection are controlled by the autonomic nervous system. The authors referred to this as the vascular phase of erection. However, rigidity is related to the muscle tone of the striated bulbospongiosus and ischiocavernosus muscles, which are innervated by somatic motor fibers of the pudendal nerve. The authors referred to this mechanism as the muscular phase of penile erection.

In a subsequent experiment using six dogs and six monkeys, Junemann, et al. performed electrical stimulation of the cavernous, pudendal, and hypogastric nerves. [See Junemann, et al. "Neurophysiology of penile erection." *Urol Res* 1989;17(4):213-7.] Arterial flow, intracorporeal pressure, and venous restriction during single and combined neurostimulation confirmed that initiation and maintenance of erection is a parasympathetic phenomenon. Penile rigidity, however, was only achieved with additional pudendal nerve stimulation, resulting in muscular compression of the blood-distended cavernous bodies. Subsidence of erection was confirmed to primarily be under sympathetic control, due to inhibition of smooth muscle relaxation. The authors concluded that penile erection is dependent upon three neurophysiological mechanisms: the parasympathetic "vascular mechanism" mediated by the cavernous nerves, the somatic motor "muscular mechanism" mediated by the pudendal nerves, and the sympathetic "inhibitory mechanism" mediated by the hypogastric nerves.

As indicated above, the present invention is directed to a method for treating erectile dysfunction or other sexual dysfunction (e.g., emission or ejaculation dysfunction) by applying stimulation and/or infused stimulating substances to nerves supplying the penis to, e.g., activate/stimulate the pudendal nerve. Stimulation may be facilitated by an implantable signal generator and electrode and/or an implantable pump and infusion outlet. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

Herein, stimulating drugs comprise medications and other pharmaceutical compounds, anesthetic agents, synthetic or natural hormones, neurotransmitters, interleukins, cytokines, lymphokines, chemokines, growth factors, neural depolarizing agents, and other intracellular and intercellular chemical signals and messengers, and the like. Certain hormones, neurotransmitters, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

Figure 4A:
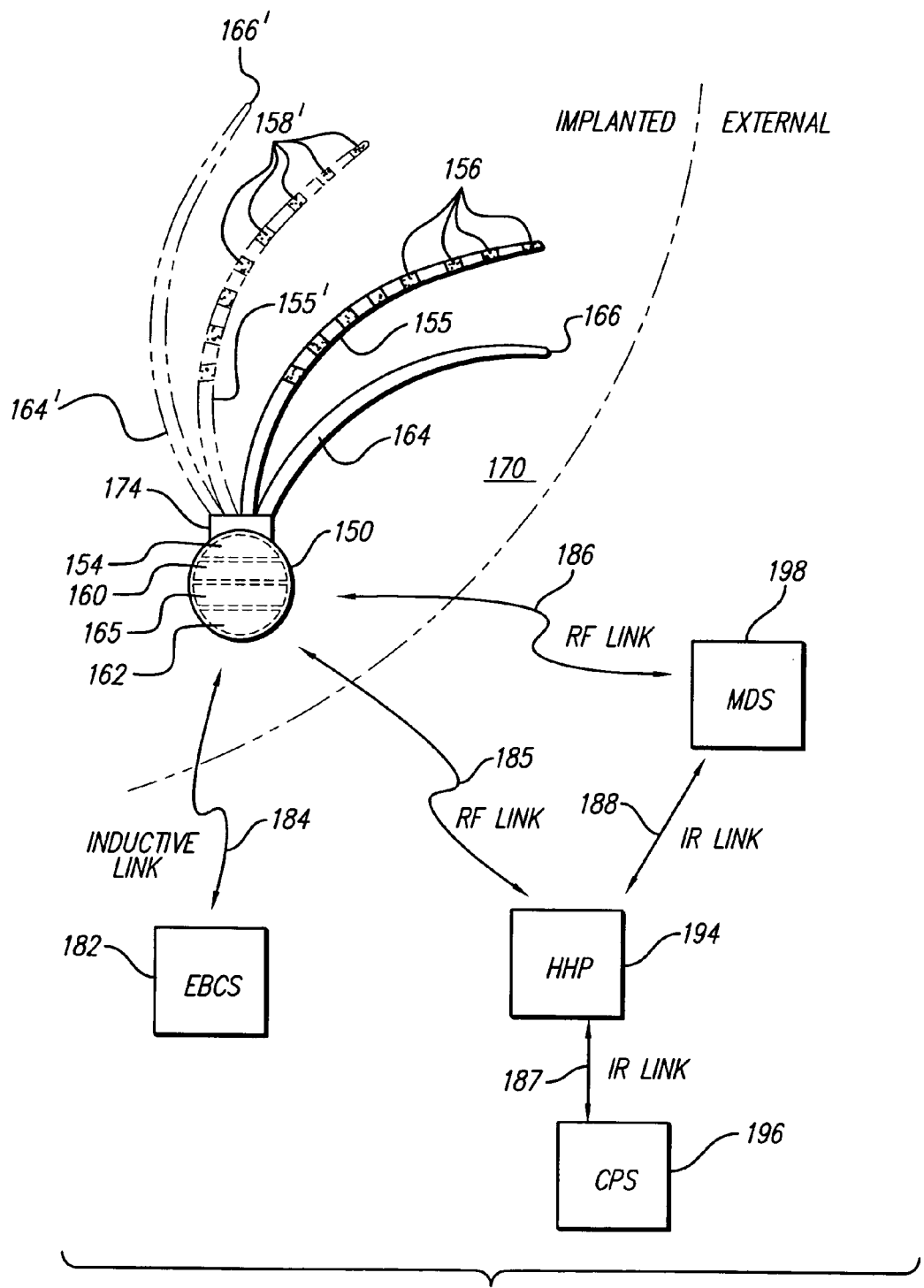
FIG. 4A illustrates internal and external components of certain embodiments of the invention.

The treatment may be provided by a system control unit (SCU) comprising an implantable pump that is coupled to a catheter having a discharge portion for infusing therapeutic dosages of the one or more drugs to a treatment site, such as shown in FIG. 4A. As seen in the embodiments depicted in FIG. 4A, SCU 150 may be surgically implanted, for instance, in the thorax, abdomen, or above the buttocks, while one or more catheters 164 attached to SCU 150 run subcutaneously in a surgically-created tunnel to the target site. Optionally, one or more electrode leads 155 may also be attached to SCU 150, with the electrodes tunneled to the target site. SCU 150, in the configuration of FIG. 4A, may conform to the profile of surrounding tissue(s) and/or bone(s), and is small and compact. This may minimize pressure applied to the skin or other tissue, which pressure may result in skin erosion or infection. In various embodiments as depicted in FIG. 4A, SCU 150 has a diameter of about 75 mm, or only about 65 mm, or even less than about 55 mm. In such configurations, SCU thickness may be about 10-12 mm, or even less than 10 mm. Small size and recessed placement of the SCU and catheter(s) and/or lead(s) decreases the likelihood of erosion of the overlying skin, and minimizes any cosmetic impact.

Figure 4B:
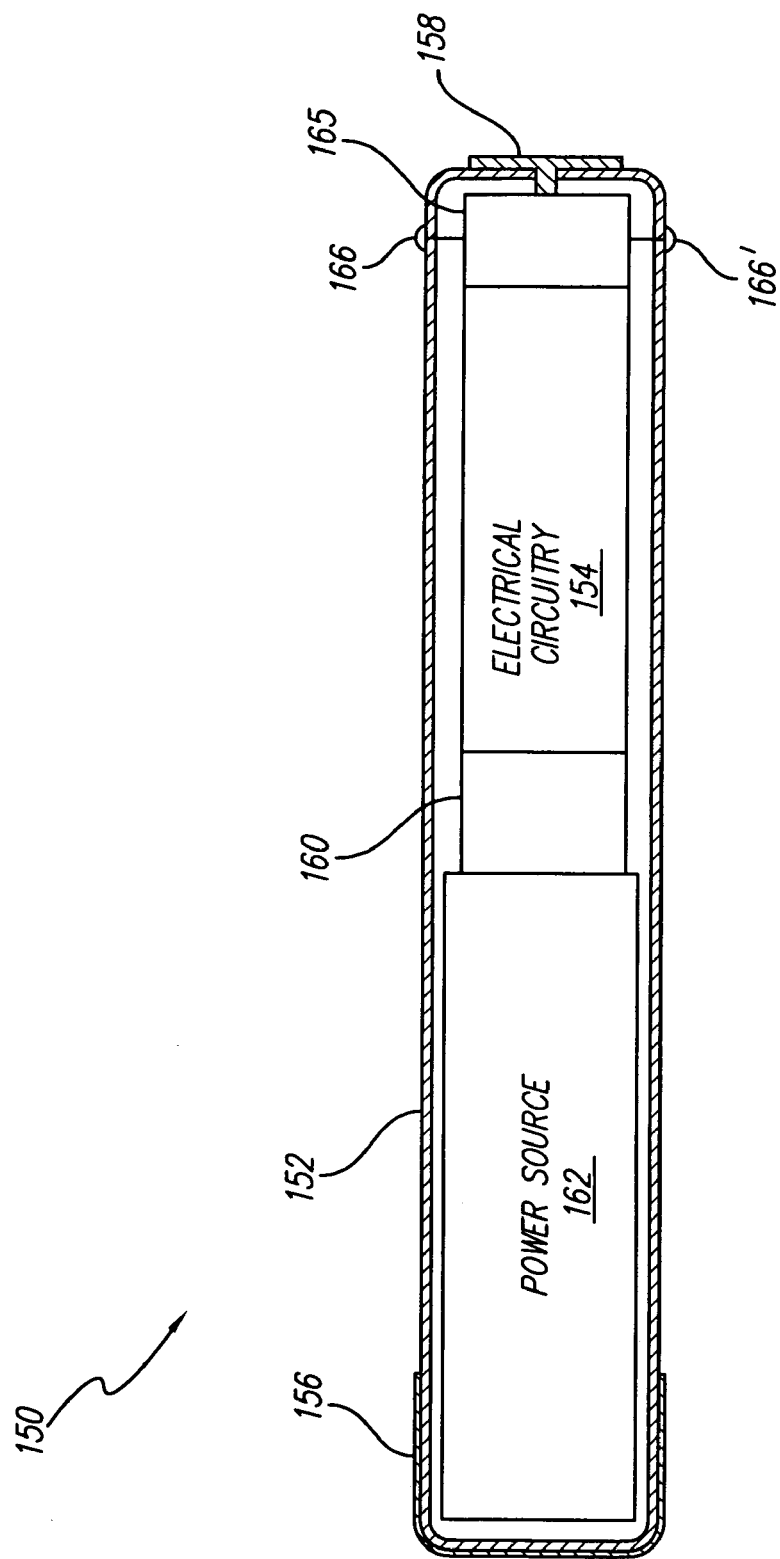
FIGS. 4B, 4C, and 4D show possible configurations of an implantable microstimulator of the present invention.
Figure 4C:
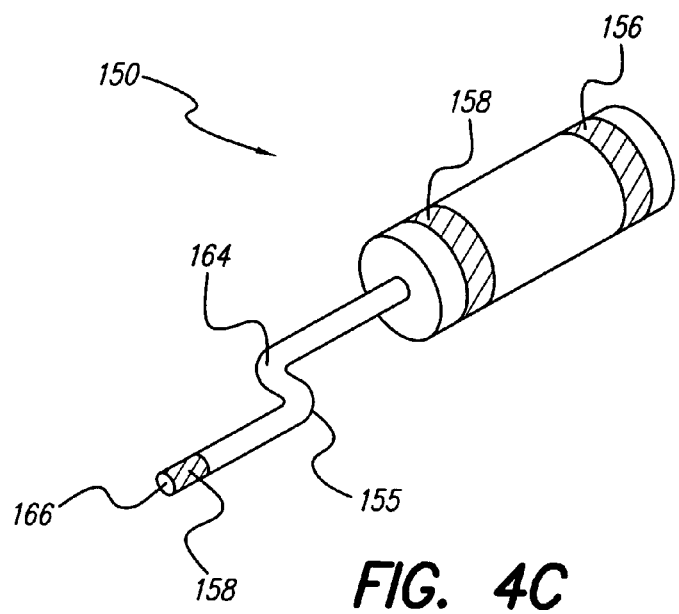
Figure 4D:
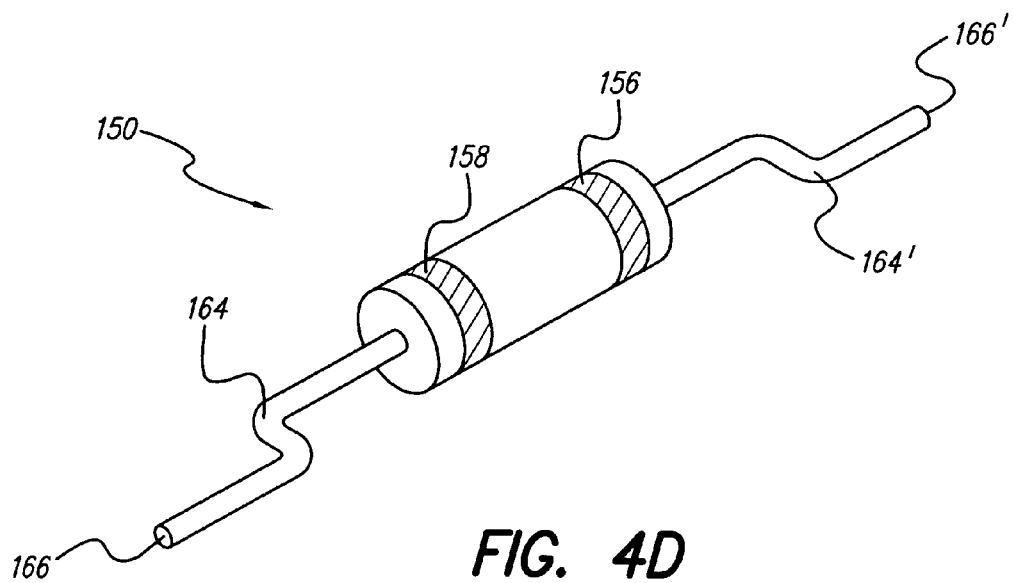

Additionally or alternatively, a small implantable device with infusion outlets, as shown in FIGS. 4B-4D, may be implanted at or near the treatment site. Such a device is taught in U.S. patent application Ser. No. 10/057,144, filed Jan. 24, 2002, which application is incorporated herein by reference.

The treatment may additionally or alternatively comprise electrical stimulation provided by an SCU that is or includes an implantable signal generator connected to an electrode(s) for electrically stimulating a treatment site. The signal generator may be coupled to a lead with electrode(s) positioned at the treatment site, such as shown in FIG. 4A, or may be a small implantable device, such as a BION® microstimulator or the like, implanted at or near the treatment site. The following documents describe various details associated with the manufacture, operation, and use of BION implantable microstimulators, and are all incorporated herein by reference:

| Application/Patent/ Publication No. | Filing/Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 6,185,452 | Issued Feb. 6, 2001 | Battery-Powered Patient Implantable Device |
| U.S. Pat. No. 6,164,284 | Issued Dec. 26, 2000 | System of Implantable Devices For Monitoring and/or Affecting Body Parameters |
| U.S. Pat. No. 6,208,894 | Issued Mar. 27, 2001 | System of Implantable Devices For Monitoring and/or Affecting Body Parameters |
| U.S. Pat. No. 6,054,017 | Issued Apr. 18, 2000 | Improved Implantable Microstimulator and Systems Employing Same |
| | published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781-790. |

For instance, to treat erectile dysfunction, a microminiature stimulator SCU 150, such as a BION microstimulator, illustrated, e.g., in FIG. 4B, may be attached to or implanted adjacent to the pudendal nerve 120. Alternatively or additionally, one or more infusion outlets 166/166' may infuse medications to stimulate the pudendal nerve 120. Such stimulation of the pudendal nerve, by electrical stimulation and/or stimulating medication, may be combined with stimulation of other structures, such as one or both cavernous nerves 108 and 112.

Certain configurations of implantable stimulator 150 are sufficiently small to permit placement near the structures to be stimulated. As used herein, "near" and "adjacent" mean as close as reasonably possible to the target(s), including touching the target(s), but in general, may be as far as about 150 mm from the target(s). In accordance with the present invention, a single SCU 150 may be implanted, or two or more SCUs may be implanted to achieve greater stimulation of all targeted nerve fibers (e.g., all branches of the greater and lesser cavernous nerves).

As shown in FIGS. 4B-4D, SCU 150 may be a capsule 152 containing electrical circuitry 154 connected to electrodes 156 and 158 at either end of the capsule. As detailed in the referenced patents, electrodes 156 and 158 generally comprise a stimulating electrode (to be placed close to the target tissue) and an indifferent electrode (for completing the circuit). Other configurations of device 150 are possible, as is evident from the above-referenced patents and as described further below.

Capsule 152 preferably has a diameter no greater than about 4-5 mm, more preferably only about 3.5 mm, and most preferably less than 3.5 mm. Capsule length is preferably no greater than about 3040 mm, more preferably only about 20-30 mm, and most preferably less than 20 mm. The shape of the microstimulator may be determined by the structure of the desired target, the surrounding area, and the method of implantation. A thin, elongated cylinder, as shown in FIGS. 4B-4D, is one possible configuration, but other shapes, such as disks, spheres, and helical structures, are possible, as are additional catheters, infusion outlets, leads, and/or electrodes.

Microstimulator SCU 150 is preferably implanted with a surgical tool such as a tool specially designed for the purpose, or with a hypodermic needle, or the like. Alternatively, device 150 may be implanted via conventional surgical methods (e.g., via a small incision), or may be placed using endoscopic or laparoscopic techniques. A more complicated surgical procedure may be required, e.g., for fixing the device in place.

In certain embodiments of the instant invention, SCU 150 includes infusion outlets 166/166' built into or slightly protruding from the SCU case, as shown in FIG. 4B. Optional electrodes 156/158 may be leadless electrodes built into or attached to the SCU case, as shown in FIGS. 4B-4D. As seen in FIGS. 4C and 4D, microstimulator SCU 150 may additionally or alternatively include infusion outlet(s) 166/166' located at the ends of short, flexible catheter(s) 164/164' and/or leads 155/155' which may optionally include electrode(s) 156/158 as described in U.S. patent application Ser. No. 09/624,130, filed Jul. 24, 2000, which is incorporated herein by reference in its entirety. The use of such catheters or leads permits, among other things, infused drugs and/or electrical stimulation to be directed more locally to targeted tissue(s) a short distance from the surgical fixation of the bulk of the implantable microstimulator SCU 150, while allowing most elements of microstimulator SCU 150 to be located in a more surgically convenient site. This minimizes the distance traversed and the surgical planes crossed by the device and any catheter(s)/lead(s). In most uses of this invention, the catheter(s)/lead(s) are no longer than about 150 mm.

SCU 150 (which herein refers to implantable pumps, pump/IPG combinations, microstimulators for drug and/or electrical stimulation, and/or other alternative devices described herein, and sometimes referred to simply as device 150 or stimulator 150) may contain at least one pump 165 for storing and dispensing one or more drugs through outlet(s) 166/166' and/or catheter(s) 164/164'. When a catheter is used, it includes at least one infusion outlet 166, usually positioned at least at a distal end, while a proximal end of the catheter is connected to SCU 150.

In the case of treatment additionally constituting electrical stimulation, in some embodiments such as depicted in FIG. 4A, electrode(s) 156 are carried on lead 155 having a proximal end coupled to SCU 150, via connector 174 if necessary. As known in the art, the lead contains insulated wires electrically connecting electrodes 156 to SCU 150. SCU 150 contains electrical components 154 that produce electrical stimulation pulses that travel through the wires of lead 155 and are delivered to electrodes 156, and thus to the tissue surrounding electrodes 156.

According to some embodiments of the invention, such as depicted in FIG. 4A, at least one catheter 164 is attached to SCU 150, via a suitable connector 174, if necessary. One or more optional leads 155 include at least one electrode 156, and may include as many as sixteen or more electrodes 156. Additional catheter(s) 164' and/or leads 155' may be attached to SCU 150. Hence, FIG. 4A shows (in phantom lines) a second catheter 164', and a second lead 155', having electrodes 158 thereon, also attached to SCU 150. Similarly, the SCUs 150 of FIGS. 4B, 4C, and 4D have outlets 166, 166' for infusing a stimulating drug(s) and optional electrodes 156, 158 for applying electrical stimulation.

Substantially cylindrical catheter(s) 164 and lead(s) 155 of certain embodiments of the present invention may be less than 5 mm in diameter, or even less than about 1.5 mm in diameter. In embodiments using one or more paddle-shaped leads, lead(s) 155 may be less than 15 mm in width, and less than 1.5 mm in thickness. Electrodes 156, 158 on leads 155, 155' may be arranged as an array, for instance, as two or more collinear electrodes, or even as four or more collinear electrodes, or they may not be collinear. A tip electrode may also be supplied at the distal end of one or more leads.

In some embodiments using optional electrical stimulation, SCU 150 is programmable to produce either monopolar electrical stimulation, e.g., using the SCU case as an indifferent electrode, or bipolar electrical stimulation, e.g., using one of the electrodes as an indifferent electrode. Some embodiments of SCU 150 have at least four channels and drive up to sixteen electrodes or more.

To protect the electrical components inside SCU 150, some or all of the case of the SCU may be hermetically sealed. Glass, ceramic, or other material that provides a hermetic package that excludes water vapor but permits passage of electromagnetic fields used to transmit data and/or power may be used. For additional protection against, e.g., impact, the case may be made of metal (e.g., titanium) or ceramic, which materials are also, advantageously, biocompatible. In addition, SCU 150 may be configured to be Magnetic Resonance Imaging (MRI) compatible. Electrodes 156/158, when used, may be made of a noble or refractory metal or compound, such as platinum, iridium, tantalum, titanium, titanium nitride, niobium or alloys of any of these, in order to avoid corrosion or electrolysis which could damage the surrounding tissues and the device.

SCU 150 contains, when necessary and/or desired, circuitry 154 for receiving data and/or power from outside the body by inductive, radio-frequency (RF), or other electromagnetic coupling. In some embodiments, circuitry 154 includes an inductive coil for receiving and transmitting RF data and/or power, an integrated circuit (IC) chip for decoding and storing stimulation parameters and generating drug or electrical stimulation pulses (either intermittent or continuous), and additional discrete electronic components required to complete the electronic circuit functions, e.g. capacitor(s), resistor(s), coil(s), and the like.

Some embodiments of SCU 150 also include a power source and/or power storage device 162. Possible power options for a stimulation device of the present invention, described in more detail below, include but are not limited to an external power source coupled to stimulator 150, e.g., via an RF link; a self-contained power source utilizing any suitable means of generation or storage of energy (e.g., a primary battery, a replenishable or rechargeable battery such as a lithium ion battery, an electrolytic capacitor, a super- or ultracapacitor, or the like); and if the self-contained power source is replenishable or rechargeable, means of replenishing or recharging the power source (e.g., an RF link, an optical link, a thermal link, or other energy-coupling link).

SCU 150 also includes, when necessary and/or desired, a programmable memory 160 for storing set(s) of data, stimulation, and/or control parameters. Among other things, memory 160 may allow electrical and/or drug stimulation and/or control parameters to be adjusted to settings that are safe and efficacious with minimal discomfort for each individual. Different parameters and/or medications may provide therapeutic advantages for various forms of erectile dysfunction and other forms of sexual dysfunction. For instance, some patients may respond favorably to intermittent stimulation, while others may require continuous stimulation to treat their dysfunction. In some embodiments, drug stimulation and electrical stimulation parameters are controlled independently, e.g., continuous drug stimulation and no electrical stimulation. However, in some instances, they may advantageously be coupled, e.g., electrical stimulation may be programmed to occur only during drug infusion.

In addition, different stimulation parameters and/or medications may have different effects on erectile function and response. Therefore, parameters and/or medications may be chosen to target specific neural populations and/or to exclude others, or to increase neural activity in specific neural populations and/or to decrease neural activity in others. For example, excitatory neurotransmitters (e.g., acetylcholine, glutamate, glutamate receptor agonist(s), dopamine, norepinephrine, epinephrine, serotonin), agonists thereof (e.g., acetylcholine receptor agonist such as bethanechol), and agents that act to increase levels of an excitatory neurotransmitter(s) (e.g., edrophonium, Mestinon) generally have an excitatory effect on neural tissue, while inhibitory neurotransmitters (e.g., dopamine, glycine, and gamma-aminobutyric acid, a.k.a. GABA), agonists thereof (e.g., benzodiazepines, such as diazepam, or barbiturates), and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. prazosin, metoprolol) and agents that decrease levels of excitatory neurotransmitter(s) (e.g., acetylcholinesterase) may inhibit neural activity.

In addition, electrical stimulation typically has an excitatory effect, leading to increased neural activity of surrounding neural tissue, when applied at relatively low frequencies (i.e., less than about 100 Hz). Conversely, an inhibitory effect, and decreased neural activity, is typical of relatively high frequency electrical stimulation (i.e., greater than about 100 Hz). As used herein, excitatory stimulation is stimulation (which can be electrical or drug stimulation) that leads to increased activity in surrounding tissue, while inhibitory stimulation is the stimulation that leads to decreased activity of the surrounding tissue.

In embodiments such as shown in FIG. 4A, SCU 150 includes a rechargeable battery as a power source/storage device 162. The battery is recharged, as required, from an external battery charging system (EBCS) 182, typically through an inductive link 184. In these embodiments, SCU 150 includes a processor and other electrical circuitry 154 that allow it to generate stimulation pulses that are applied to the patient 170 through outlet(s) 166 and optional electrode(s) 156 in accordance with a program and stimulation parameters stored in programmable memory 160. As stated earlier, stimulation pulses of drugs include various types and/or rates of infusion, such as intermittent infusion, infusion at a constant rate, and bolus infusion.

According to certain embodiments of the invention, an SCU operates independently. According to various other embodiments of the invention, an SCU operates in a coordinated manner with other SCU(s), other implanted device(s), and/or other device(s) external to the patient's body. For instance, an SCU may control or operate under the control of another implanted SCU(s), other implanted device(s), and/or other device(s) external to the patient's body. An SCU may communicate with other implanted SCUs, other implanted devices, and/or devices external to a patient's body via, e.g., an RF link, an ultrasonic link, a thermal link, and/or an optical link. Specifically, an SCU may communicate with an external remote control (e.g., patient and/or physician programmer) that is capable of sending commands and/or data to an SCU and that is preferably capable of receiving commands and/or data from an SCU.

For example, as depicted in FIG. 4A, some embodiments of SCU 150 of the present invention may be activated and deactivated, programmed and tested through a hand held programmer (HHP) 194 (which may also be referred to as a patient programmer and may be, but is not necessarily, hand held), a clinician programming system (CPS) 196 (which may also be hand held), and/or a manufacturing and diagnostic system (MDS) 198 (which may also be hand held). HHP 194 may be coupled to SCU 150 via an RF link 185. Similarly, MDS 198 may be coupled to SCU 150 via another RF link 186. In a like manner, CPS 196 may be coupled to HHP 194 via an infra-red link 187; and MDS 198 may be coupled to HHP 194 via another infra-red link 188. Other types of telecommunicative links, other than RF or infra-red may also be used for this purpose. Through these links, CPS 196, for example, may be coupled through HHP 194 to SCU 150 for programming or diagnostic purposes. MDS 198 may also be coupled to SCU 150, either directly through RF link 186, or indirectly through the IR link 188, HHP 194, and RF link 185.

Figure 5:
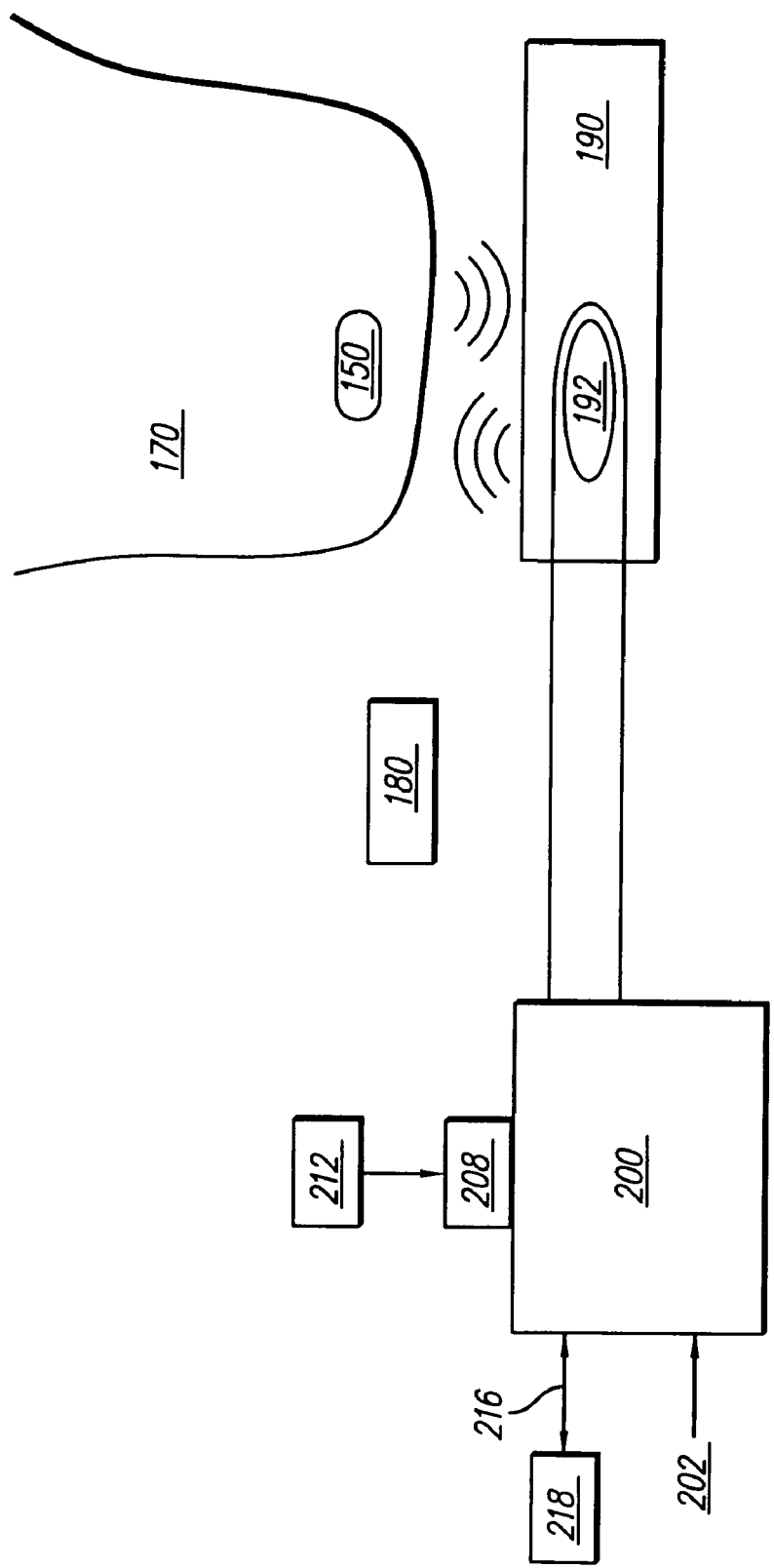
FIG. 5 illustrates external components of various embodiments of the invention.

In certain embodiments, using, for example, a microstimulator SCU 150 as describe above and as illustrated in FIG. 5, the patient 170 switches the implantable stimulator 150 on and off by use of controller 180, which is preferably (but not necessarily) handheld. For instance, a drug or drug agent that promotes an erection acutely may be delivered on demand when the patient indicates such delivery is requires, such as via depression of an implanted button or via a remote control 180 that is in communication with the SCU 150. SCU 150 may be operated by controller 180 by any of other various means, including sensing the proximity of a permanent magnet located in controller 180, sensing RF transmissions from controller 180, or the like.

Additional/alternative external components for programming and/or providing power to various embodiments of implantable stimulator 150 are also illustrated in FIG. 5. When communication with such an SCU 150 is desired, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which may receive power 202 from a conventional power source. External appliance 200 contains manual input means 208, e.g., a keypad, whereby the patient 170 or a caregiver 212 may request changes in electrical and/or drug stimulation parameters produced during the normal operation of SCU 150. In these embodiments, manual input means 208 include various electro-mechanical switches and/or visual display devices that provide the patient and/or caregiver with information about the status and prior programming of SCU 150.

Alternatively or additionally, external electronic appliance 200 is provided with an electronic interface means 216 for interacting with other computing means 218, such as by a serial interface cable or infrared link to a personal computer or to a telephone modem or the like. Such interface means 216 may permit a clinician to monitor the status of the implant and prescribe new stimulation parameters from a remote location.

One or more of the external appliance(s) may be embedded in a seat cushion, mattress cover, pillow, garment, or the like. Other possibilities exist, including a belt, strap, patch, or other structure(s) that may be affixed to the patient's body or clothing. External appliances may include a package that can be, e.g., worn on the belt, may include an extension to a transmission coil affixed, e.g., with a Velcro® band or an adhesive, or may be combinations of these or other structures able to perform the functions described herein.

In order to help determine the amount and/or type(s) of stimulating drug(s) and/or the strength and/or duration of electrical stimulation required to produce the desired therapeutic effect, in some embodiments, a patient's response to and/or need for treatment is sensed. For example, a pressure sensor in or around the penis or its internal structures, such as a penile tumescence sensor or penile arteriole pressure sensor, may sense changes in response to stimulation. Other measures of the state of the patient may additionally or alternatively be sensed, e.g., cavernous nerve firing rate; intercavernous pressure; joint angle; muscle activity (e.g., EMG); nerve activity (e.g., ENG); and/or other measures mentioned below.

For example, when an SCU 150 is implanted adjacent to pudendal nerve 120, the signals from a pressure sensor built into microstimulator 150 may be recorded. Alternatively, an "SCU" dedicated to sensory processes communicates with an SCU providing stimulation pulses. The implant circuitry 154 may, if necessary, amplify and transmit these sensed signals, which may be analog or digital. Other methods of determining the required stimulation include observing the stimulation required to initiate and maintain erection, as well as measuring neurotransmitter levels and/or their associated breakdown product levels, nitric oxide and/or breakdown product levels, hormone levels, or other substances, such as dopamine levels, interleukins, cytokines, lymphokines, chemokines, growth factors, enzymes, medication and/or other drug levels, and/or levels of any other bloodborne substance(s), and/or changes in one or more of these may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). Other methods are mentioned herein, and yet others will be evident to those of skill in the field upon review of the present disclosure. The sensing may occur during stimulation (e.g., infusion) or during a temporary suspension of stimulation. The sensed information may be used to control stimulation parameters in a closed-loop manner.

For instance, in several embodiments of the present invention, a first and second "SCU" are provided. The second "SCU" periodically (e.g. once per minute) records a level of muscle activity (or neural activity, etc.), which it transmits to the first SCU. The first SCU uses the sensed information to adjust drug and/or electrical stimulation parameters according to an algorithm programmed, e.g., by a physician. For example, the amplitude of stimulation may be increased in response to decreased penile arteriole pressure or decreased intracavernous pressure. More preferably, one stimulator performs both the sensing and stimulating functions, as discussed in more detail presently.

While an SCU may also incorporate means of sensing dysfunction, it may alternatively or additionally be desirable to use a separate or specialized implantable device to record and telemeter physiological conditions/responses in order to adjust drug infusion and/or electrical stimulation parameters. This information may be transmitted to an external device, such as external appliance 190, or may be transmitted directly to implanted stimulator(s) 150. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with microstimulator 150 to accomplish, potentially among other things, one or more of the following functions:

Function 1: If necessary, transmit electrical power from the external electronic appliance 200 via appliance 190 to the stimulator 150 in order to power the device and/or recharge the power source/storage device 162. External electronic appliance 200 may include an automatic algorithm that adjusts drug and/or electrical stimulation parameters automatically whenever the implantable stimulator(s) 150 is/are recharged.

Function 2: Transmit data from the external appliance 200 via the external appliance 190 to the implantable stimulator 150 in order to change the parameters of drug and/or electrical stimulation used by stimulator 150.

Function 3: Transmit sensed data indicating a need for treatment or in response to stimulation from stimulator 150 (e.g., pressure, joint angle, electromyographical activity, level of a blood-borne substance(s), or other activity) to external appliance 200 via the external appliance 190.

Function 4: Transmit data indicating state of the implantable stimulator 150 (e.g., battery level, drug level, stimulation parameters, etc.) to external appliance 200 via external appliance 190.

In another example, a treatment for erectile dysfunction is carried out according to the following sequence of procedures:

1. Anatomical landmarks that identify the course of the pudendal nerve 120 and/or any other nerves to be stimulated (e.g., pudendal nerve branches) are located;
2. Optionally, the presence and/or functionality of the nerve(s) is confirmed at the site(s), e.g., via electrical stimulation or drug infusion;
3. An SCU 150 is implanted so that its infusion outlet(s) 166/166' and possibly also electrodes 156 and/or 158 are adjacent to pudendal nerve 120.
   If necessary or desired, one or more additional infusion outlet(s) 166' and/or electrodes 156/158 (from the same or additional SCU(s) 150) may be implanted adjacent to other nerve fibers, such as the greater cavernous nerve 108 and/or lesser cavernous nerve 112.
4. Using Function 2 described above (i.e., transmitting data) of external electronic appliance 200 and external appliance 190, SCU 150 is commanded to infuse a fixed bolus of an excitatory neurotransmitter agonist, e.g., acetylcholine, or a neural depolarizing agent, e.g., succinylcholine or the sodium channel activator veratridine, possibly while producing a series of excitatory electrical stimulation pulses, possibly with gradually increasing amplitude.
5. After each infusion pulse, or series of pulses, or at some other predefined interval, any change in arteriole pressure in arteries supplying the penis (and/or intra-cavernosal pressure) is sensed, preferably by one or more electrodes 156 and 158 or sensors. These responses are converted to data and telemetered out to external electronic appliance 200 via Function 3.
6. From the response data received at external appliance 200 from SCU 150, or from some other assessment, the stimulus threshold for obtaining a response is determined and is used by a clinician acting directly 212 or by other computing means 218 to transmit the desired drug and/or electrical stimulation parameters to SCU 150 in accordance with Function 2. Alternatively, external appliance 200 makes the proper adjustments automatically, and transmits the proper stimulation parameters to SCU 150. In yet another alternative, SCU 150 adjusts stimulation parameters automatically based on the sensed response.

7. When patient 170 desires to invoke drug infusion and/or electrical stimulation to instigate erection, he employs controller 180 to set the SCU 150 in a state where it delivers a prescribed stimulation pattern from a predetermined range of allowable stimulation patterns.

8. To allow his penis to return to a flaccid state, patient 170 employs controller 180 to turn off SCU 150.

9. Periodically, the patient or caregiver recharges the power source/storage device 162 of SCU 150, if necessary, in accordance with Function 1 described above (i.e., transmit electrical power).

For the treatment of any of the various types of sexual dysfunction, it may be desirable to modify or adjust the algorithmic functions performed by the implanted and/or external components, as well as the surgical approaches. For example, in some situations, it may be desirable to employ more than one SCU 150, each of which could be separately controlled by means of a digital address. Multiple channels and/or multiple patterns of drug and/or electrical stimulation might thereby be programmed by the clinician and controlled by the patient in order to, for instance, deal with complex or multiple dysfunctions such as may occur as a result of spinal cord injury and neurodegenerative disorders.

In some embodiments discussed earlier, SCU 150, or a group of two or more SCUs, is controlled via closed-loop operation. A need for and/or response to stimulation is sensed via SCU 150, or by an additional SCU (which may or may not be dedicated to the sensing function), or by another implanted or external device. If necessary, the sensed information is transmitted to SCU 150. In some cases, the sensing and stimulating are performed by one SCU. In some embodiments, the parameters used by SCU 150 are automatically adjusted based on the sensed information. Thus, the electrical and/or drug stimulation parameters are adjusted in a closed-loop manner to provide stimulation tailored to the need for and/or response to electrical and/or drug stimulation.

Figure 6:
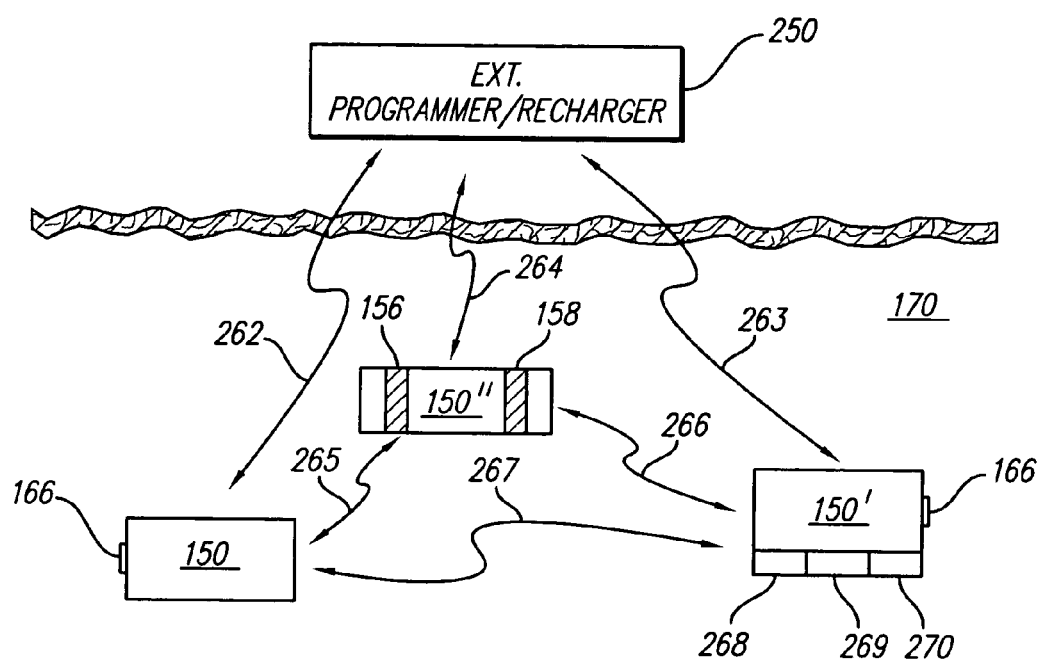
FIG. 6 depicts a system of implantable devices that communicate with each other and/or with external control/programming devices.

For instance, as shown in the examples of FIG. 6, a first SCU 150, implanted beneath the skin of the patient 170, provides a first medication or substance; a second SCU 150' provides a second medication or substance; and a third SCU 150" provides electrical stimulation via electrodes 156 and 158. As mentioned earlier, the implanted devices may operate independently or may operate in a coordinated manner with other similar implanted devices, other implanted devices, or other devices external to the patient's body, as shown by the control lines 262, 263 and 264 in FIG. 6. That is, in accordance with certain embodiments of the invention, the external controller 250 controls the operation of each of the implanted devices 150, 150' and 150". According to various embodiments of the invention, an implanted device, e.g. SCU 150, may control or operate under the control of another implanted device(s), e.g. SCU 150' and/or SCU 150". That is, a device made in accordance with the invention may communicate with other implanted stimulators, other implanted devices, and/or devices external to a patient's body, e.g., via an RF link, an ultrasonic link, a thermal link, an optical link, or the like. Specifically, as illustrated in FIG. 6, SCU 150, 150', and/or 150", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects, clinical variables, or other indicators of the state of the patient, such as arteriole pressure, pressure in the corpus cavernosum and/or corpus spongiosum, ENG, or the like. The stimulator additionally or alternatively incorporates second means 269 for sensing neurotransmitter levels and/or their associated breakdown product levels, nitric oxide level and/or its associated breakdown product levels, medication levels and/or other drug levels, hormone levels and/or changes in these or other substances in the blood plasma, local interstitial fluid, and/or cerebrospinal fluid. The stimulator additionally or alternatively incorporates third means 270 for sensing electrical current levels and/or waveforms supplied by another source of electrical energy, if necessary. Sensed information may be used to control infusion and/or electrical parameters in a closed loop manner, as shown by control lines 265, 266, and 267. Thus, the sensing means may be incorporated into a device that also includes drug and/or electrical stimulation, or the sensing means (that may or may not have stimulating means), may communicate the sensed information to another device(s) with stimulating means.

According to one therapeutic alternative, the dysfunction may be treated with increased excitement of the parasympathetic input to the penis. Relatively low-frequency electrical stimulation (e.g., less than about 100 Hz) is likely to produce such excitement. Therefore, as described above, stimulation may be applied to one or more of the cavernous nerves. Alternatively or additionally, a stimulator(s) 150 may be implanted adjacent to parasympathetic targets deeper in the patient's body, such as the proximal portion of cavernous nerves 108 and 112, the prostatic plexus 107, the pelvic splanchnic nerves 100, or the second, third, and/or fourth sacral nerves (S2, S3, S4).

According to another therapeutic alternative, the dysfunction may be treated by inhibiting excitement of sympathetic nerve input to the penis. In this case, relatively high-frequency electrical stimulation (e.g., greater than about 100 Hz) is likely to produce such inhibition. Thus, a microstimulator(s) may also/instead be implanted adjacent to one or more of the hypogastric nerves 178, certain nerves of the inferior hypogastric plexus 104 or its branches, or the sympathetic ganglia from which they arise, in order to inhibit sympathetic input that retards erection.

According to some embodiments of the invention, the dysfunction may be treated by increasing excitement of the somatic motor input to the penis. For instance, certain drug stimulation increases activity of efferent fibers of the pudendal nerve 120 and/or of one or more pudendal nerve branches (together, known as the pudendal nerves), thereby acting to increase the muscle tone of the striated bulbospongiosus and ischiocavernosus muscles and enhancing the somatic motor "muscular mechanism" of erection. Infusion with a neural depolarizing agent (e.g., veratridine), an excitatory neurotransmitter (e.g., acetylcholine), an excitatory neurotransmitter agonist (e.g., acetylcholine receptor agonist), an agent that acts to increase levels of an excitatory neurotransmitter, an inhibitory neurotransmitter antagonist, an agent that acts to decrease levels of an inhibitory neurotransmitter and/or an agent that acts to cause a portion of an axon to generate an action potential is likely to produce such increased activity. Some embodiments of the invention utilize electrical stimulation or combine electrical stimulation with drug stimulation. In such embodiments, excitatory stimulation to cause increased activity is likely to be produced by relatively low-frequency electrical stimulation (e.g., less than about 100 Hz).

As described earlier, this drug and/or electrical stimulation may be applied to the pudendal nerve 120, including the portion in the pudendal canal, and/or any of the distal branches of the pudendal nerve, such as the dorsal nerve of the penis 122, to treat erectile dysfunction. Such stimulation may be combined with stimulation of other structures described earlier, including one or more cavernous nerves (such as greater cavernous nerve 108 and lesser cavernous nerve 112), the prostatic plexus 107, the pelvic splanchnic nerves 100, and/or one or more sacral nerves (S2, S3, S4). For example, the greater cavernous nerve 108 and pudendal nerve 120 may be stimulated at the same time, or in that sequence.

In yet another alternative, placement of the microstimulator(s) may be chosen to effect emission (discharge of semen) or ejaculation (ejection of semen in orgasm). While parasympathetic input is responsible for erection, sympathetic impulses are required for ejaculation. As stated earlier, the sympathetic nervous system originates in the thoracic and lumbar regions of the spinal cord. It is believed that a portion of the sympathetic outflow leaving the spinal cord at the first and second lumbar segments travels through the lower lumbar or pelvic parts of the sympathetic trunk, then via the inferior hypogastric plexus, to arrive at the vas deferens, the seminal vesicles, and the prostate. Therefore, stimulating certain branches of the inferior hypogastric plexus that innervate the prostate, seminal vesicles, and vas deferens may lead to emission and/or ejaculation. Alternatively or additionally, stimulation of the pelvic splanchnic nerves leading to the prostate may cause emission and/or ejaculation.

Furthermore, sensing means described earlier may be used to orchestrate first the activation of SCU(s) targeting nerves that cause erection, then the SCU(s) targeting nerves and/or using different means, e.g., applying different drugs, that maintain erection, and then, when appropriate, the SCU(s) targeting nerves and/or using different means, that cause ejaculation. For instance, excitatory stimulation of the sympathetic nerves going to the prostate, or stimulation of the prostate directly (e.g., electro-ejaculation), can cause ejaculation. Alternatively, this orchestration may be programmed, or triggered by the user, and not based on a sensed condition. For example, when a button is pushed, stimulation of parasympathetic nerves is turned off and stimulation of sympathetic nerves is turned on, causing ejaculation.

By applying the methods of treatment taught herein to the analogous neuromuscular structures of the female anatomy (e.g., stimulating nerves of the uterovaginal plexus and branches thereof rather than the prostatic plexus and branches thereof, stimulating the pudendal nerve of the female or branches thereof, such as the dorsal nerve of the clitoris rather than the dorsal nerve of the penis), the treatment may be adapted for female sexual dysfunction, e.g., affecting clitoral engorgement, increased vaginal secretions, and/or treatment of vaginismus and/or dyspareunia.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with sexual dysfunction comprising:
   providing at least one stimulator having at least one infusion outlet for infusing at least one stimulating drug;
   implanting the at least one stimulator with the at least one infusion outlet adjacent to at least one nerve supplying somatic motor input to the penis;
   providing operating power to the at least one stimulator;
   using at least one external appliance to transmit stimulation parameters to the at least one stimulator;
   receiving and storing the stimulation parameters; and
   delivering the at least one stimulating drug to nerve fibers adjacent to the at least one infusion outlet in accordance with the stimulation parameters;
   wherein the at least one stimulator has a size and shape suitable for placement of the at least one infusion outlet adjacent to the at least one nerve supplying somatic motor input to the penis.

2. The method of claim 1 wherein the at least one stimulating drug increases activity of at least one nerve supplying somatic motor input to the penis.

3. The method of claim 2 wherein the at least one nerve supplying somatic motor input to the penis comprises at least one of the pudendal nerves.

4. The method of claim 3 wherein the at least one pudendal nerve is at least one of the pudendal nerve and the dorsal nerve of the penis.

5. The method of claim 1 further comprising implanting at least one infusion outlet adjacent to at least one nerve providing autonomic innervation of the penis.

6. The method of claim 5 wherein the at least one nerve providing autonomic innervation of the penis comprises one or more of the cavernous nerves, the nerves of the prostatic plexus, the nerves of the branches of the prostatic plexus, the nerves of the uterovaginal plexus, the nerves of the branches of the uterovaginal plexus, the pelvic splanchnic nerves, the second, third, and fourth sacral nerves, the hypogastric nerves, the sympathetic ganglia from which the hypogastric nerves arise, the hypogastric nerves, the nerves of the inferior hypogastric plexus, and the nerves of the branches of the inferior hypogastric plexus.

7. The method of claim 1 wherein the implantable stimulator further comprises at least one sensor.

8. The method of claim 7 wherein the sensed condition is used to adjust the stimulation parameters.

9. The method of claim 8 wherein the parameter adjustment is performed using the at least one external appliance.

10. The method of claim 8 wherein the parameter adjustment is performed by the implantable stimulator.

11. A method for treating a patient with sexual dysfunction comprising:
    providing at least one stimulator having at least one infusion outlet;
    implanting the at least one stimulator adjacent to at least one nerve innervating the reproductive organs of a patient;
    providing operating power to the at least one stimulator;
    using at least one external appliance to transmit stimulation parameters to the at least one stimulator;

receiving and storing the stimulation parameters;
generating stimulation pulses in accordance with the stimulation parameters; and
delivering the stimulation pulses to tissue adjacent to the at least one stimulator.

12. The method of claim 11 wherein the at least one nerve supplies parasympathetic input to the reproductive organs.

13. The method of claim 12 wherein the at least one nerve comprises at least one nerve of the cavernous nerves, the prostatic plexus, branches of the prostatic plexus, the uterovaginal plexus, branches of the uterovaginal plexus, the pelvic splanchnic nerves, the second third, and fourth sacral nerves, and the hypogastric nerves.

14. The method of claim 11 wherein the at least one nerve supplies sympathetic input to the reproductive organs.

15. The method of claim 14 wherein the at least one nerve comprises one or more of the sympathetic ganglia from which the hypogastric nerves arise, the hypogastric nerves, the nerves of the inferior hypogastric plexus, and the nerves of the branches of the inferior hypogastric plexus.

16. The method of claim 11 wherein the at least one nerve effects emission or ejaculation.

17. The method of claim 16 wherein the at least one nerve comprises at least one nerve of the branches of the inferior hypogastric plexus that innervate at least one of the prostate, seminal vesicles, and vas deferens.

18. The method of claim 17 wherein the at least one nerve comprises at least one of the pelvic splanchnic nerves.

19. A method for treating a patient with at least one sexual dysfunction, comprising the steps of:
providing at least one means for stimulating tissue;
implanting at least a portion of the at least one stimulating means adjacent to at least one nerve innervating at least one reproductive organ;
providing operating power to the at least one stimulating means;
transmitting stimulation parameters to the at least one stimulating means using at least one external appliance;
receiving and storing the stimulation parameters; and
stimulating tissue adjacent to the at least one infusion outlet;
wherein the stimulating means includes at least one infusion outlet.

20. The method of claim 19 wherein the stimulating means is no more than about 150 mm from the at least one nerve to be stimulated.

* * * * *